United States Patent
Li et al.

(10) Patent No.: US 9,775,530 B2
(45) Date of Patent: Oct. 3, 2017

(54) FOLEY CATHETER WITH RING ELECTRODES

(71) Applicant: MEDTRONIC XOMED, INC., Jacksonville, FL (US)

(72) Inventors: Wenjeng Li, Saint Johns, FL (US); Dwayne Yamasaki, St. Augustine, FL (US); Marc Zimmermann, Santa Barbara, CA (US); Kevin Mauch, Windsor, CA (US)

(73) Assignee: Medtronic Xomed, Inc., Jacksonville, FL (US)

( * ) Notice: Subject to any disclaimer, the term of this patent is extended or adjusted under 35 U.S.C. 154(b) by 209 days.

(21) Appl. No.: 14/531,578

(22) Filed: Nov. 3, 2014

(65) Prior Publication Data

US 2015/0126839 A1    May 7, 2015

Related U.S. Application Data

(60) Provisional application No. 61/898,915, filed on Nov. 1, 2013.

(51) Int. Cl.
| | |
|---|---|
| *A61B 5/04* | (2006.01) |
| *A61N 1/05* | (2006.01) |
| *A61B 5/00* | (2006.01) |
| *A61M 25/00* | (2006.01) |
| *A61M 25/10* | (2013.01) |
| *A61N 1/36* | (2006.01) |

(52) U.S. Cl.
CPC ........ *A61B 5/04001* (2013.01); *A61B 5/4041* (2013.01); *A61B 5/6852* (2013.01); *A61M 25/0017* (2013.01); *A61M 25/10* (2013.01); *A61N 1/05* (2013.01); *A61N 1/0521* (2013.01); *A61N 1/36007* (2013.01); *A61B 2562/043* (2013.01); *A61M 2210/1089* (2013.01)

(58) Field of Classification Search
CPC .. A61B 5/04001; A61B 5/6852; A61N 1/0521
See application file for complete search history.

(56) References Cited

U.S. PATENT DOCUMENTS

| | | | |
|---|---|---|---|
| 4,063,548 A | * | 12/1977 | Klatt ................. A61B 5/04882 600/546 |
| 5,775,331 A | | 7/1998 | Raymond et al. |
| 6,259,945 B1 | | 7/2001 | Epstein et al. |
| | | | (Continued) |

FOREIGN PATENT DOCUMENTS

| | | |
|---|---|---|
| WO | 99/18851 A1 | 4/1999 |
| WO | 2008/153726 A2 | 12/2008 |

OTHER PUBLICATIONS

International Search Report and Written Opinion dated Sep. 8, 2015 re PCT/US2014/063697, 11 pages.

(Continued)

*Primary Examiner* — Lee S Cohen
(74) *Attorney, Agent, or Firm* — Dicke, Billig & Czaja, PLLC

(57) ABSTRACT

An apparatus for monitoring a nerve includes a Foley type catheter having an exterior surface, and first and second pairs of ring electrodes formed on the exterior surface of the Foley catheter. Each of the first and second pairs of ring electrodes is configured to perform at least one of stimulating the nerve and recording nerve activity.

21 Claims, 6 Drawing Sheets

(56) References Cited

U.S. PATENT DOCUMENTS

| | | | |
|---|---|---|---|
| 6,517,534 B1 * | 2/2003 | McGovern | A61B 18/1485 606/28 |
| 6,535,759 B1 | 3/2003 | Epstein et al. | |
| 7,079,882 B1 * | 7/2006 | Schmidt | A61B 5/4041 600/373 |
| 7,894,913 B2 * | 2/2011 | Boggs | A61N 1/36107 607/118 |
| 8,083,685 B2 | 12/2011 | Fagin et al. | |
| 8,204,597 B2 * | 6/2012 | Gerber | A61N 1/36007 607/40 |
| 2007/0283969 A1 | 12/2007 | Yamasaki et al. | |
| 2008/0319348 A1 * | 12/2008 | Nakajima | A61B 5/053 600/585 |
| 2009/0248034 A1 | 10/2009 | Dolan et al. | |
| 2010/0036471 A1 | 2/2010 | Dolan et al. | |
| 2010/0145222 A1 | 6/2010 | Brunnett et al. | |
| 2011/0301662 A1 | 12/2011 | Bar-Yoseph et al. | |
| 2013/0030262 A1 | 1/2013 | Burnett et al. | |
| 2013/0131743 A1 | 5/2013 | Yamasaki et al. | |
| 2013/0165916 A1 * | 6/2013 | Mathur | A61B 18/18 606/33 |

OTHER PUBLICATIONS

J. Physiol (1968), 196, pp. 563-577, The Identification and Characteristics of Sacral Parasympathetic Preganglionic Neurones, by W.C. de Groat and R.W. Ryall; received Nov. 7, 1967.

Foley Catheter—Wikipedia, http://en.wikipedia.orgiwiki/Foley_catheter, last modified Aug. 9, 2013, 4 pages.

Biomedical Reviews 2003; 14: pp. 23-50, ISSN 1310-392X, Functional Electric Stimulation for Sensory and Motor Functions: Progress and Problems, Dimiter Prodanov, Enrico Marani and Jan Holsheimer.

* cited by examiner

FOLEY CATHETER WITH RING ELECTRODES

CROSS-REFERENCE TO RELATED APPLICATIONS

This application claims priority under 35 U.S.C. §119(e)(1) to U.S. Provisional Patent Application Ser. No. 61/898,915, filed Nov. 1, 2013, entitled "Foley Catheter Electrode For IONM And Post Up Recovery Stimulation", and the entire teachings of which are incorporated herein by reference.

BACKGROUND

Conventionally, a radical prostatectomy is performed by cutting an incision at the base of the pelvic bone to gain access to the prostate. Once visible, the prostate is cut from the surrounding tissue and removed. Because the area around the prostate is rich in nerves and muscles that support sexual and urinary functions, a radical prostatectomy can cause severe side effects, including sexual dysfunction and incontinence. Although laparoscopic and robotic surgery have shown promising potential in reducing erectile dysfunction as a side effect of prostate gland removal, erectile dysfunction does still occur.

In many invasive medical procedures, such as a radical prostatectomy, steps can be taken to preserve healthy surrounding tissues while performing the procedure on a target tissue. A surgeon attempts to guard against unintentional damage to surrounding nerves while excising tissue. This damage may result from direct trauma (e.g. an incision) or "blind" trauma, such as stretching, torsion, compression, ischemia, thermal damage, electrical damage, or other surgical manipulations. Blind damage is of particular concern because the damage may be cumulative over the course of the surgery but may not be recognizable by the surgeon during the surgery.

One conventional technique of preserving the nerve includes the surgeon periodically applying a stimulation probe at the nerve and simultaneously measuring the neurogenic response from an associated innervated muscle via electromyography or other techniques. Accordingly, each time the surgeon desires to check the health or integrity of the nerve, the surgeon will maneuver the probe to contact the nerve, and apply the stimulation signal. After measuring and observing the response to the stimulus, the surgeon removes the probe from contact with the nerve.

Unfortunately, this conventional technique can lead to many inconsistencies. For example, it is difficult to establish accurate information about the response of an unimpaired nerve because the stimulation probe is placed in a slightly different location each time it is applied, resulting in a slightly different stimulus to the nerve. This contact variability in applying the stimulus leads to a slightly different response pattern. Accordingly, the slightly different locations of stimulation tend to cloud ascertainment of a normal or typical response of the innervated muscle (when the nerve is not impaired) and also cloud identification of a response signal that corresponds to an impairment or disturbance of the nerve. Moreover, because the stimulation probe is applied intermittently, there is no assurance whether the response signal is being measured at the time that the nerve is being impaired or being measured at the time the nerve is not being impaired.

In addition to radical prostatectomy surgeries, similar issues arise in other pelvic surgeries (e.g., hysterectomy, bladder cancer, colorectal surgery, ureter, vasectomy, etc.). Accordingly, the conventional techniques used during medical procedures to monitor the health of a nerve fall short of the consistency and accuracy that would be desirable to reliably ascertain the integrity of the nerve during surgery.

SUMMARY

One embodiment is directed to an apparatus for monitoring a nerve. The apparatus includes a Foley type catheter having an exterior surface, and first and second pairs of ring electrodes formed on the exterior surface of the Foley catheter. Each of the first and second pairs of ring electrodes is configured to perform at least one of stimulating the nerve and recording nerve activity.

DETAILED DESCRIPTION

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

Some embodiments of the present disclosure are directed to electrically monitoring a nerve during a surgical procedure on a target tissue that is in the vicinity of the nerve. In general terms, the method includes applying stimulation signals to a nerve adjacent to the target tissue via electrodes on a Foley type catheter. In some embodiments, a neurogenic response is recorded (e.g., measured) at the nerve as a direct nerve potential.

In some embodiments, the term neurogenic refers to a neural-related response or activity initiated by natural neural processes (i.e., spontaneous nerve activity, or nerve activity evoked by natural activation of its axonal membrane or receptors), while in other embodiments, the term neurogenic refers to a neural-related response or activity initiated by an external stimulus, such as, but not limited to an evoked potential stimulus. In yet other embodiments, the term neurogenic refers to a neural-related response or activity caused by both a naturally neural process and an external stimulus. In some embodiments, the term nerve refers to neuro structures in general or some specific neuro structures, including (but not limited to) one or more of an entire nerve, a nerve fiber, multiple nerve fibers, an axon, a spatial grouping of axons, or a functional grouping of axons within the nerve.

By positioning a Foley catheter with nerve electrodes (of one of the embodiments of the present disclosure) relative to a target nerve and monitoring the ensuing neurogenic response, a surgeon can achieve and maintain a hands-free, automatic continuous (or substantially continuous) monitoring of the health and integrity of a nerve in a reliably consistent manner during a surgical procedure.

One embodiment is directed to a Foley catheter with electrodes for intraoperative neurophysiological monitoring (IONM) and post-operative and intraoperative recovery stimulation. In one embodiment, the Foley catheter includes a plurality of pairs of electrodes for recording nerve action potentials during a pelvic surgery, such as a radical prostatectomy, hysterectomy, bladder cancer, colorectal surgery, ureter, vasectomy, or other pelvic surgery.

Figure 1:
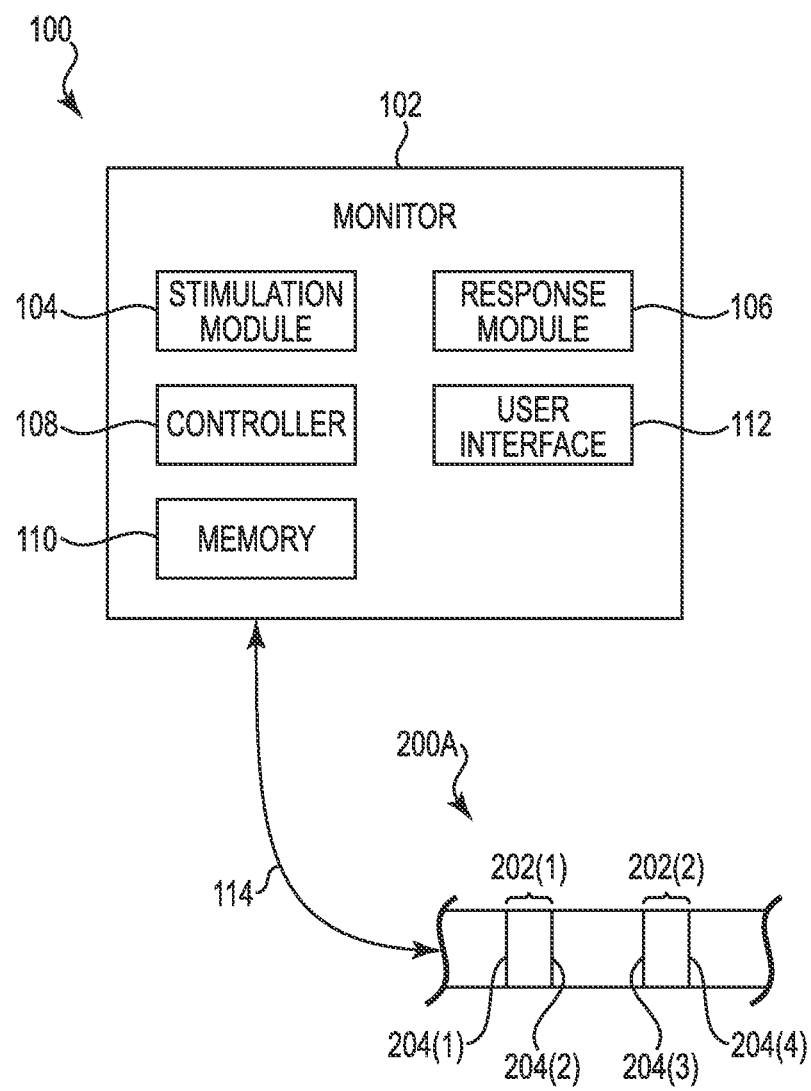
FIG. 1 is a block diagram illustrating a nerve stimulation and monitoring system according to one embodiment.

FIG. 1 is a block diagram illustrating a nerve stimulation and monitoring system 100 according to one embodiment. System 100 includes monitor 102 and Foley type catheter 200A. Monitor 102 includes stimulation module 104, response module 106, controller 108, memory 110, and user interface 112. Foley catheter 200A includes a plurality of pairs 202(1)-202(2) of electrodes (collectively referred to as electrode pairs 202). Electrode pair 202(1) includes electrodes 204(1) and 204(2), and electrode pair 202(2) includes electrodes 204(3) and 204(4). Electrodes 204(1)-204(4) are collectively referred to as electrodes 204. In one embodiment, electrode pair 202(2) comprises bipolar stimulation electrodes, and electrode pair 202(1) comprises bipolar response electrodes. In other embodiments, electrode pairs 202 can comprise any combination of stimulation electrodes and response electrodes, including all stimulation electrodes or all response electrodes. Stimulation may also be provided via a probe.

In operation according to one embodiment, the stimulation module 104 of the monitor 102 applies a stimulation signal to a nerve via stimulation electrode pair 202(2), while response module 106 of monitor 102 measures a neurogenic response signal at the nerve via measuring a direct action potential with the response electrode pair 202(1). The response is communicated to a surgeon via user interface 112 of the monitor 102. Accordingly, by using monitor 102, a surgeon can determine the relative health and function of a nerve by stimulating that nerve and measuring a corresponding neurogenic response. In some embodiments, one or more of electrodes pairs 202 record nerve activity evoked by a separate stimulating bipolar probe. In other embodiments, one or more of the electrode pairs 202 stimulates nerves, and a separate bipolar probe is used to record the evoked nerve activity.

In one embodiment, controller 108 of monitor 102 comprises one or more processing units and associated memories configured to generate control signals directing the operation of monitor 102. In particular, in response to or based upon commands received via user interface 112 and/or instructions contained in the memory 110 associated with controller 108, controller 108 generates control signals directing operation of stimulation module 104 and/or response module 106.

The term "processing unit", as used herein, means a presently developed or future developed processing unit that executes sequences of instructions contained in a memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage, as represented by memory 110. In other embodiments, hard wired circuitry may be used in place of or in combination with software instructions to implement the functions described. For example, controller 108 may be embodied as part of one or more application-specific integrated circuits (ASICs). Unless otherwise specifically noted, the controller 108 is not limited to any specific combination of hardware circuitry and software, nor limited to any particular source for the instructions executed by the processing unit.

In one embodiment, each of the electrodes 204 is a ring electrode that completely surrounds a circumference of the Foley catheter 200A. In one embodiment, each electrode pair 202 is a bipolar electrode pair, with one of the electrodes 204 in the pair being an anode, and the other electrode 204 in the pair being a cathode. When the electrodes 204(1) and 204(2) are configured as an anode and a cathode, this electrode pair 202(1) can deliver bipolar stimulation to nerves proximate a target site, or provide bipolar recording of nerve activity proximate the target site. When the electrodes 204(3) and 204(4) are configured as an anode and a cathode, this electrode pair 202(2) can deliver bipolar stimulation to nerves proximate a target site, or provide bipolar recording of nerve activity proximate the target site. In one embodiment, a second one of the electrode pairs 202 (e.g., electrode pair 202(2)) is configured to stimulate nerves, and a first one of the electrode pairs 202 (e.g., electrode pair 202(1)) is spaced apart from the second electrode pair along the Foley catheter 200A and is configured to measure the action potential of the nerves resulting from the stimuli of the second electrode pair. Action potential is the electrical activity developed in a nerve cell during activity (e.g., induced by a stimulus from the second electrode pair).

Electrodes 204 are communicatively coupled to monitor 102 via communication link 114. In one embodiment, communication link 114 includes signal wires or conductors that are operatively coupled to the electrodes 204 to drive nerve stimulation, record nerve activity, and/or otherwise provide a signal between the electrodes 204 and monitor 102. In one embodiment, the signal wires extend through the catheter 200A to a proximal end of the catheter 200A where the signal wires can be operatively connected to the monitor 102. In one embodiment, monitor 102 comprises a Nerve Integrity Monitor ("NIM") made available by Medtronic Xomed of Jacksonville, Fla., which provides intraoperative nerve monitoring capabilities using visual and/or audible indications of nerve activity.

The electrode pairs 202 according to one embodiment are positioned to accommodate most prostate sizes, by placing one of the pairs 202 close to the membranous urethra. The membranous urethra is the level where the nerves innervating the external genitalia of both sexes exit the pelvis, and thus are an optimal location for recording or stimulating these nerves. In addition, having more than one pair of electrodes allows for stimulating and recording the nerves. Also, the electrode pairs 202 allow for recording spontaneous nerve activity during the surgery. They also allow for stimulating the nerves during surgical recovery for therapeutic facilitation of nerve improvement and recovery in the event of iatrogenic nerve injury or irritation. In some embodiments, electrode pairs 202 are used for spontaneous recording during surgical dissection.

Figure 2:
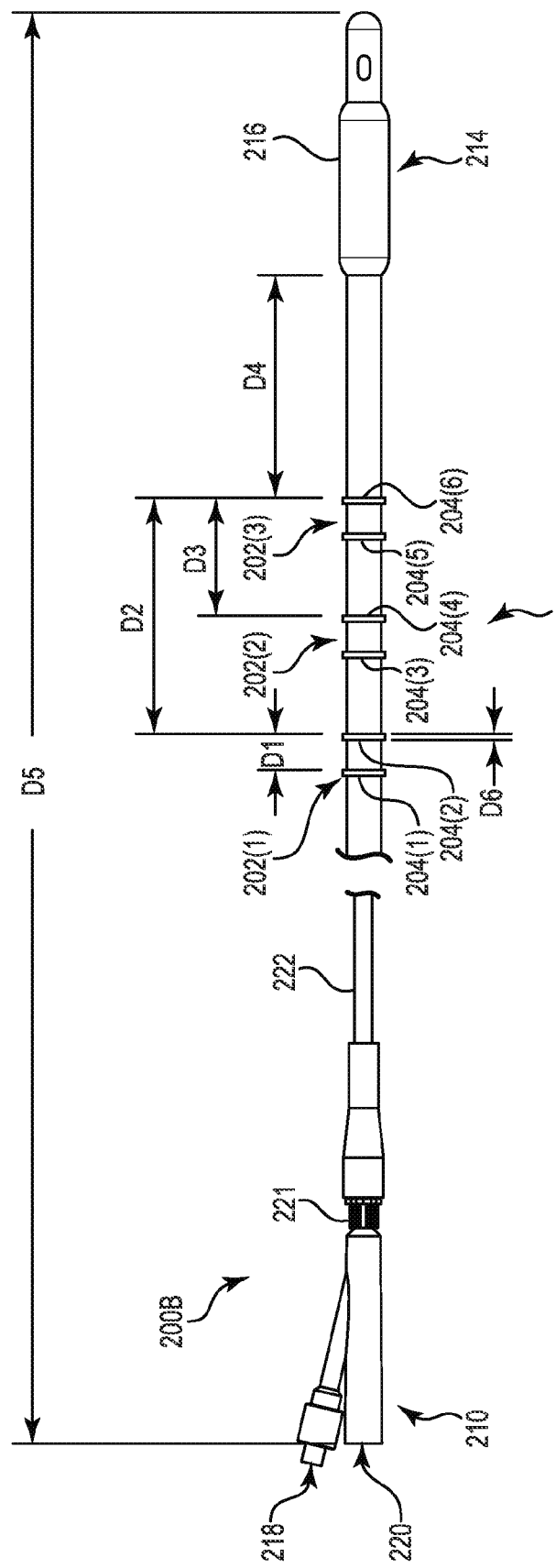
FIG. 2 is a diagram illustrating a Foley catheter with three electrode pairs that is suitable for use with the system shown in FIG. 1 according to one embodiment.

FIG. 2 is a diagram illustrating a Foley catheter 200B with three electrode pairs that is suitable for use with the system 100 shown in FIG. 1 according to one embodiment. A catheter, such as catheter 200B, may be understood to have various sections according to their disposition when the catheter is inserted into a human subject. Foley catheter 200B has a proximal portion 210 that remains outside of the human subject, a central portion 212 that traverses the urethra, and a distal portion 214 that resides in the urinary bladder. Foley catheter 200B comprises a flexible tube 222 that is passed through the urethra and into the bladder. The Foley catheter 200B is held in place by an inflatable balloon 216 that stabilizes the device in place, and prevents inadvertent withdrawal from the bladder. The Foley catheter 200B includes at least two separated lumens 218 and 220 along its length. Lumen 220 is open at both ends and serves as a conduit that drains urine from the bladder, and lumen 218 serves as an air or fluid conduit that allows the balloon 216 to be controllably inflated when it lies inside the bladder, in order to stop it from slipping out. The signal wires 221 of communication link 114 (FIG. 1) may be disposed in a lumen of catheter 200B that allows communication of sensing signals between distally disposed electrodes 204 and the proximal portion 210 of the catheter 200B.

Foley catheter 200B includes three pairs 202(1)-202(3) of electrodes (collectively referred to as electrode pairs 202). Electrode pair 202(1) includes electrodes 204(1) and 204(2), and electrode pair 202(2) includes electrodes 204(3) and 204(4), and electrode pair 202(3) includes electrodes 204(5) and 204(6). Electrodes 204(1)-204(6) are collectively referred to as electrodes 204. In one embodiment, the electrode pair closest to the membranous urethra is used to either stimulate or record nerve activity. In another embodiment, at least one of the electrode pairs 202 comprises bipolar stimulation electrodes, and at least one of the electrode pairs 202 comprises bipolar recording electrodes. In other embodiments, electrode pairs 202 are used in combination with a separate bipolar probe.

The individual electrodes 204 in each electrode pair 202 are longitudinally spaced apart from each other along the length of the catheter 200B by a distance, D1, which is about 5-10 mm in one embodiment. This inter-electrode distance for each electrode pair 202 optimizes the recorded signal-to-noise for periprostatic nerves based on their known conduction velocity (i.e., 0.5-30 m/sec). In other embodiments, the electrodes 204 can be spaced closer together or further apart. In various embodiments, the separation between the electrodes 204 in each electrode pair 202 is selected to enhance the signal to noise ratio for recording nerve activity for a particular type of nerve fiber (e.g., A-delta fibers, B-fibers, and/or C-fibers).

In one embodiment, the Foley catheter 200B has an overall length, D5, of about 425 mm. In one embodiment, the distance, D4, from the proximal end of the balloon 216 to the most distally disposed electrode 204(6) is about 35-40 mm. In one implementation, the distance, D4, is about 37.5 mm. In one embodiment, the pitch of the electrode pairs 202 is about 18-22 mm (e.g., the distance measured from the center point of one electrode pair 202 to the center point of an adjacent electrode pair 202). In one implementation, the pitch of the electrode pairs 202 is about 20 mm, so the distance, D3, is about 20 mm, and the distance, D2, is about 40 mm. The distance, D6, represents the lateral width of electrodes 204, which is about 1 mm in one embodiment.

Figure 3:
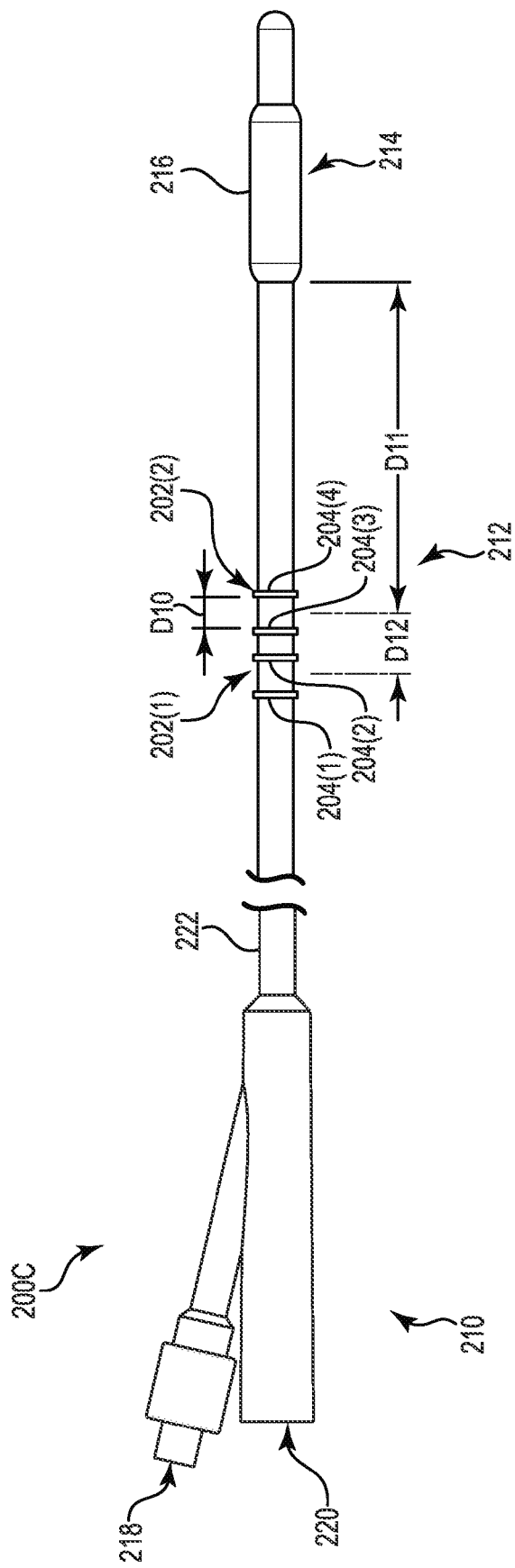
FIG. 3 is a diagram illustrating a Foley catheter with two electrode pairs that is suitable for use with the system shown in FIG. 1 according to one embodiment.

FIG. 3 is a diagram illustrating a Foley catheter 200C with two electrode pairs that is suitable for use with the system 100 shown in FIG. 1 according to one embodiment. Foley catheter 200C according to one embodiment is configured to be used for a prostate up to 5.5 cm. Foley catheter 200C has a proximal portion 210 that remains outside of the human subject, a central portion 212 that traverses the urethra, and a distal portion 214 that resides in the urinary bladder. Foley catheter 200C comprises a flexible tube 222 that is passed through the urethra and into the bladder. The Foley catheter 200C is held in place by an inflatable balloon 216 that stabilizes the device in place, and prevents inadvertent withdrawal from the bladder. The Foley catheter 200C includes at least two separated lumens 218 and 220 along its length. Lumen 220 is open at both ends and serves as a conduit that drains urine from the bladder, and lumen 218 serves as an air or fluid conduit that allows the balloon 216 to be controllably inflated when it lies inside the bladder, in order to stop it from slipping out. The signal wires of communication link 114 (FIG. 1) may be disposed in a lumen of catheter 200C that allows communication of sensing signals between distally disposed electrodes 204 and the proximal portion 210 of the catheter 200C.

Foley catheter 200C includes two pairs 202(1)-202(2) of electrodes (collectively referred to as electrode pairs 202). Electrode pair 202(1) includes electrodes 204(1) and 204(2), and electrode pair 202(2) includes electrodes 204(3) and 204(4). Electrodes 204(1)-204(4) are collectively referred to as electrodes 204. In one embodiment, at least one of the electrode pairs 202 comprises bipolar stimulation electrodes, and at least one of the electrode pairs 202 comprises bipolar recording electrodes. In other embodiments, electrode pairs 202 are used in combination with a separate bipolar probe.

The individual electrodes 204 in each electrode pair 202 are longitudinally spaced apart from each other along the length of the catheter 200C by a distance, D10, which is about 5-10 mm in one embodiment. This inter-electrode distance for each electrode pair 202 optimizes the recorded signal-to-noise for periprostatic nerves based on their known conduction velocity (i.e., 0.5-30 m/sec). In other embodiments, the electrodes 204 can be spaced closer together or further apart.

In one embodiment, the distance, D11, from the proximal end of the balloon 216 to the center of the most distally disposed electrode pair 202(2) is about 47-57 mm. In one specific implementation, the distance, D11, is about 52 mm. In one embodiment, the pitch of the electrode pairs 202 is about 8-12 mm (e.g., the distance measured from the center point of one electrode pair 202 to the center point of an adjacent electrode pair 202), so the distance, D12, is about 8-12 mm. In one specific implementation, the distance D12 is about 10 mm.

Figure 4:
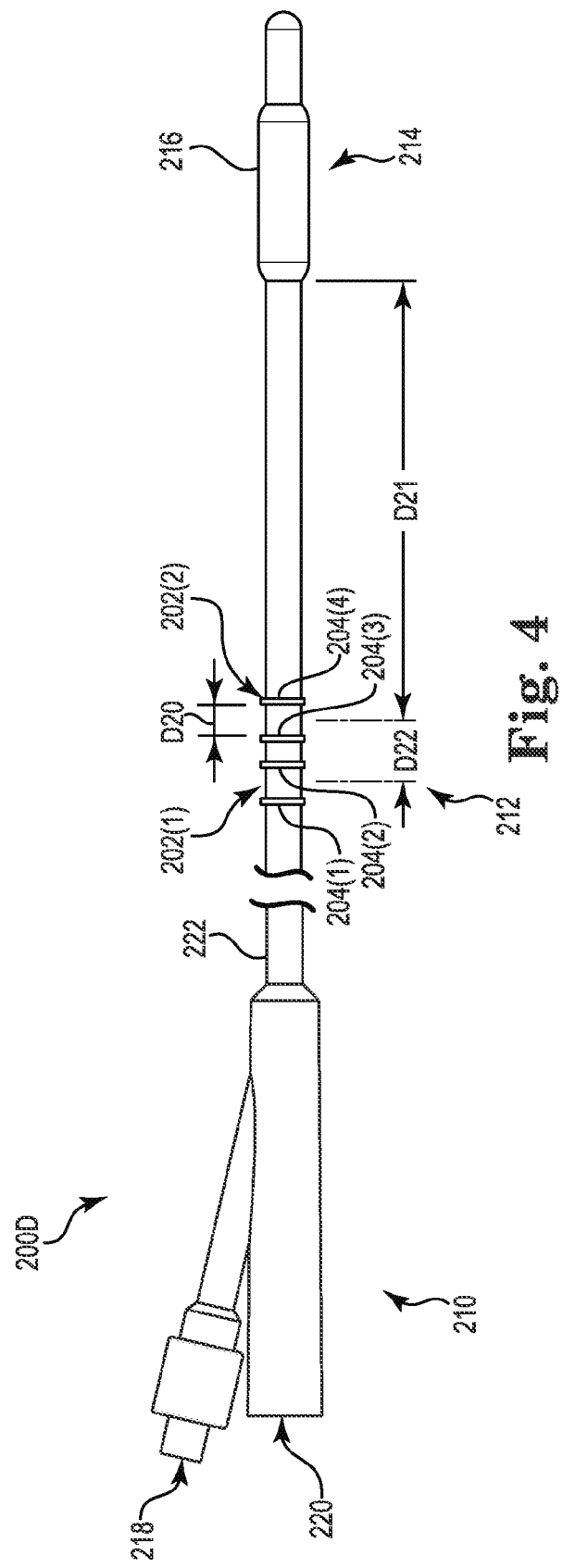
FIG. 4 is a diagram illustrating a Foley catheter with two electrode pairs that is suitable for use with the system shown in FIG. 1 according to another embodiment.

FIG. 4 is a diagram illustrating a Foley catheter 200D with two electrode pairs that is suitable for use with the system 100 shown in FIG. 1 according to another embodiment. Foley catheter 200D according to one embodiment is configured to be used for a prostate larger than 5.5 cm. Foley catheter 200D has a proximal portion 210 that remains outside of the human subject, a central portion 212 that traverses the urethra, and a distal portion 214 that resides in the urinary bladder. Foley catheter 200D comprises a flexible tube 222 that is passed through the urethra and into the bladder. The Foley catheter 200D is held in place by an inflatable balloon 216 that stabilizes the device in place, and prevents inadvertent withdrawal from the bladder. The Foley catheter 200D includes at least two separated lumens 218 and 220 along its length. Lumen 220 is open at both ends and serves as a conduit that drains urine from the bladder, and lumen 218 serves as an air or fluid conduit that allows the balloon 216 to be controllably inflated when it lies inside the bladder, in order to stop it from slipping out. The signal wires of communication link 114 (FIG. 1) may be disposed in a lumen of catheter 200D that allows communication of sensing signals between distally disposed electrodes 204 and the proximal portion 210 of the catheter 200D.

Foley catheter 200D includes two pairs 202(1)-202(2) of electrodes (collectively referred to as electrode pairs 202). Electrode pair 202(1) includes electrodes 204(1) and 204(2), and electrode pair 202(2) includes electrodes 204(3) and 204(4). Electrodes 204(1)-204(4) are collectively referred to as electrodes 204. In one embodiment, at least one of the electrode pairs 202 comprises bipolar stimulation electrodes, and at least one of the electrode pairs 202 comprises bipolar recording electrodes. In other embodiments, electrode pairs 202 are used in combination with a separate bipolar probe.

The individual electrodes 204 in each electrode pair 202 are longitudinally spaced apart from each other along the length of the catheter 200D by a distance, D20, which is about 5-10 mm in one embodiment. This inter-electrode distance for each electrode pair 202 optimizes the recorded signal-to-noise for periprostatic nerves based on their known conduction velocity (i.e., 0.5-30 m/sec). In other embodiments, the electrodes 204 can be spaced closer together or further apart.

In one embodiment, the distance, D21, from the proximal end of the balloon 216 to the center of the most distally disposed electrode pair 202(2) is about 68-78 mm. In one specific implementation, the distance, D21, is about 73 mm. In one embodiment, the pitch of the electrode pairs 202 is about 10.5-14.5 mm (e.g., the distance measured from the center point of one electrode pair 202 to the center point of an adjacent electrode pair 202), so the distance, D22, is about 10.5-14.5 mm. In one specific implementation, the distance D22 is about 12.5 mm.

Figure 5:
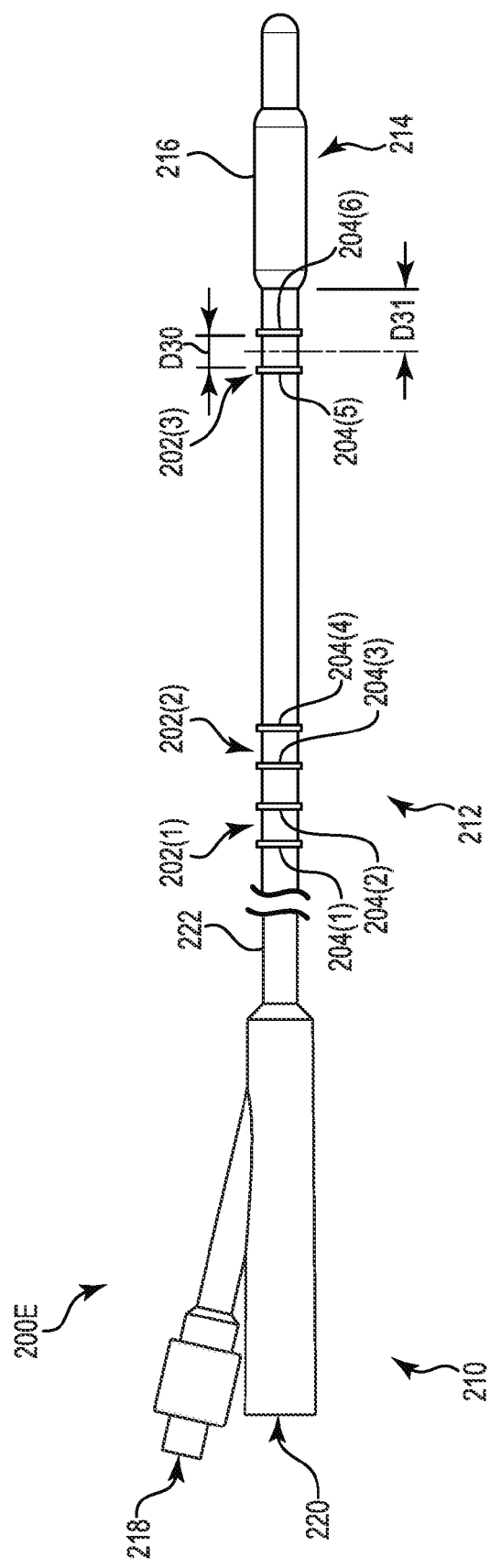
FIG. 5 is a diagram illustrating a Foley catheter with three electrode pairs that is suitable for use with the system shown in FIG. 1 according to another embodiment.

FIG. 5 is a diagram illustrating a Foley catheter 200E with three electrode pairs that is suitable for use with the system 100 shown in FIG. 1 according to another embodiment. Foley catheter 200E has a proximal portion 210 that remains outside of the human subject, a central portion 212 that traverses the urethra, and a distal portion 214 that resides in the urinary bladder. Foley catheter 200E comprises a flexible tube 222 that is passed through the urethra and into the bladder. The Foley catheter 200E is held in place by an inflatable balloon 216 that stabilizes the device in place, and prevents inadvertent withdrawal from the bladder. The Foley catheter 200E includes at least two separated lumens 218 and 220 along its length. Lumen 220 is open at both ends and serves as a conduit that drains urine from the bladder, and lumen 218 serves as an air or fluid conduit that allows the balloon 216 to be controllably inflated when it lies inside the bladder, in order to stop it from slipping out. The signal wires of communication link 114 (FIG. 1) may be disposed in a lumen of catheter 200E that allows communication of sensing signals between distally disposed electrodes 204 and the proximal portion 210 of the catheter 200E.

Foley catheter 200D includes three pairs 202(1)-202(3) of electrodes (collectively referred to as electrode pairs 202). Electrode pair 202(1) includes electrodes 204(1) and 204(2), and electrode pair 202(2) includes electrodes 204(3) and 204(4), and electrode pair 202(3) includes electrodes 204(5) and 205(6). Electrodes 204(1)-204(6) are collectively referred to as electrodes 204. In one embodiment, at least one of the electrode pairs 202 comprises bipolar stimulation electrodes, and at least one of the electrode pairs 202 comprises bipolar recording electrodes. In other embodiments, electrode pairs 202 are used in combination with a separate bipolar probe.

The individual electrodes 204 in each electrode pair 202 are longitudinally spaced apart from each other along the length of the catheter 200E by a distance, D30, which is about 5-10 mm in one embodiment. This inter-electrode distance for each electrode pair 202 optimizes the recorded signal-to-noise for periprostatic nerves based on their known conduction velocity (i.e., 0.5-30 m/sec). In other embodiments, the electrodes 204 can be spaced closer together or further apart.

In one embodiment, the distance, D31, from the proximal end of the balloon 216 to the center of the most distally disposed electrode pair 202(3) is about 5-15 mm. In one specific implementation, the distance, D31, is about 10 mm.

Figure 6:
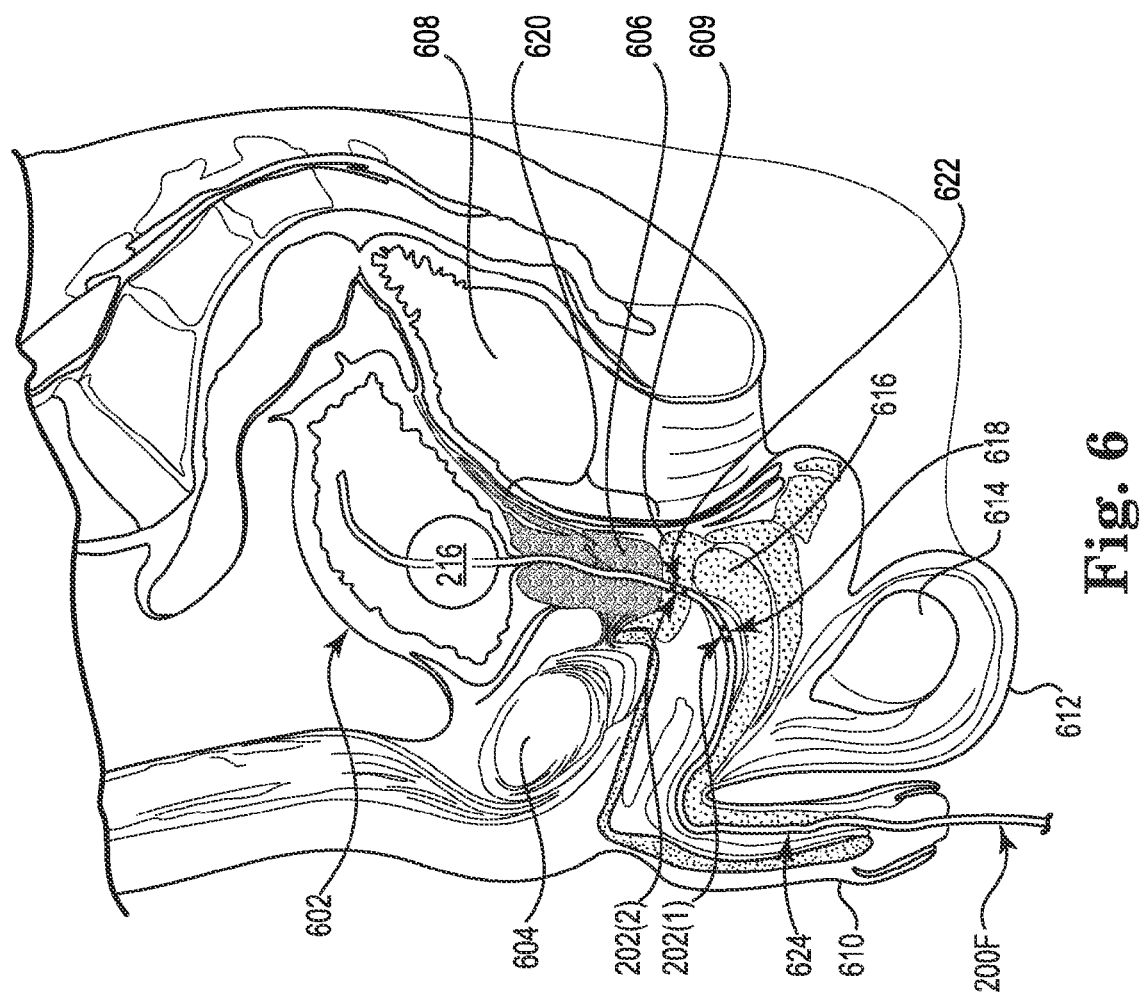
FIG. 6 is a diagram illustrating a Foley catheter with two electrode pairs that is positioned within the urethra of a human male subject according to one embodiment.

FIG. 6 is a diagram illustrating a Foley catheter 200F with two electrode pairs that is positioned within the urethra of a human male subject according to one embodiment. Foley catheter 200F is suitable for use with the system 100 shown in FIG. 1. It is noted that any of the Foley catheters 200A-200E described herein can also be positioned and function as described below with respect to Foley catheter 200F. Portions of the male subject shown in FIG. 6 include urinary bladder 602, symphysis pubis 604, prostate 606, rectum 608, urinary sphincter 609, penis 610, scrotum 612, testis 614, bulb 616, and urethra 618. There are three main sections of the male urethra 618: (1) Prostatic urethra 620 (i.e., the portion of the urethra 618 within prostate 606; (2) Membranous urethra 622 (i.e., the portion of the urethra 618 within the urinary sphincter 609; and (3) Penile urethra 624 (i.e., the portion of the urethra 618 within the penis 610).

Foley catheter 200F has a proximal portion that remains outside of the human subject, a central portion that traverses the urethra 618, and a distal portion that resides in the urinary bladder 602. Foley catheter 200F comprises a flexible tube that is passed through the urethra 618 and into the bladder 602. The Foley catheter 200F is held in place by an inflatable balloon 216 that stabilizes the device in place, and prevents inadvertent withdrawal from the bladder 602. The Foley catheter 200F includes at least two separated lumens and along its length. A first one of the lumens is open at both ends and serves as a conduit that drains urine from the bladder 602, and a second one of the lumens serves as an air or fluid conduit that allows the balloon 216 to be controllably inflated when it lies inside the bladder 602, in order to stop it from slipping out. The signal wires of communication link 114 (FIG. 1) may be disposed in a lumen of catheter 200F that allows communication of sensing signals between distally disposed electrodes and the proximal portion of the catheter 200F.

Foley catheter 200F includes two pairs 202(1)-202(2) of electrodes (collectively referred to as electrode pairs 202). In one embodiment, at least one of the electrode pairs 202 comprises bipolar stimulation electrodes, and at least one of the electrode pairs 202 comprises bipolar recording electrodes. In other embodiments, electrode pairs 202 are used in combination with a separate bipolar probe.

The individual electrodes in each electrode pair 202 are longitudinally spaced apart from each other along the length of the catheter 200F by a distance of about 5-10 mm in one embodiment. This inter-electrode distance for each electrode pair 202 optimizes the recorded signal-to-noise for periprostatic nerves based on their known conduction velocity (i.e., 0.5-30 m/sec). In other embodiments, the electrodes can be spaced closer together or further apart.

The Foley catheter 200F is shown in the urethra 618 with the balloon 216 inflated. The distal electrode pair 202(2) is positioned at the membranous urethra 622, and the proximal electrode pair 202(1) is positioned below the membranous urethra at the bulb 616. A large component of periprostatic nerves are autonomic nerves responsible for erection, ejaculation and continence. The membranous urethra 622 is where all the nerves innervating the external genitalia of either gender converge prior to exiting the pelvis, so it is an optimum location for nerve access from within the urethra. Note that, in FIG. 6, the distance between the proximal end of the balloon 216 and the distal electrode pair 202(2) equals the length of the prostate 606.

In one embodiment, the Foley catheter 200F is configured to stimulate the periprostatic nerves with a second electrode pair (e.g., electrode pair 202(2)) and record nerve activity with a first electrode pair (e.g., electrode pair 202(1)). In further embodiments, the first electrode pair 202(1) can be configured to provide stimulation and the second electrode pair 202(2) can be configured to record the resultant nerve activity.

The first and second electrode pairs 202(1) and 202(2) can be spaced far enough apart from one another such that the signal artifact associated with the bipolar stimulation from the second electrode pair 202(2), which is less than that which would be produced by monopolar stimulation, does not substantially engulf or otherwise interfere with the signal being recorded at the first electrode pair 202(1). The magnitude of the signal artifact at the first electrode pair 202(1) depends at least in part on the conduction velocity of the nerve fibers and the spacing between the stimulus and recording electrodes. C-fibers, B-fibers, and A-delta-fibers, such as those found in nerves, have relatively low conduction velocities (e.g., no more than 3 m/s for C-fibers, about 3-14 m/s for B-fibers, and about 12-30 m/s for A-delta fibers). As such, when the first electrode pair 202(1) is configured to record periprostatic nerve activity, the first electrode pair 202(1) can be positioned at least 10 mm spaced apart from the second electrode pair 202(2) along the longitudinal axis of the catheter 200F to reduce the signal artifact recorded by the first electrode pair 202(1). In other embodiments, the first and second electrode pairs 202(1) and 202(2) can be spaced different distances apart from one another along the longitudinal axis of the catheter 200F.

In one embodiment, system 100 (FIG. 1) is configured to automatically measure the distance between the stimulating and recording electrodes in real-time in order to calculate the nerve conduction velocity (NCV) of compound nerve action potentials (CNAPs). Knowing the nerve conduction velocity of the recorded nerves helps to identify the function of the nerves. Inter-electrode distances can be determined using a number of different technologies such as measuring tissue impedances between two sites, and time-of-flight of electromagnetic fields. Knowing the distance between the two electrodes and the latency of the evoked CNAP allows system 100 to calculate the NCV, and list the fiber types being recorded in real-time with user interface 112. This gives the surgeon information of the type of nerves being recorded (e.g., autonomic vs. somatic), which in turn is important for identifying the nerves innervating the penis.

One embodiment is directed to an apparatus for monitoring a nerve. The apparatus includes a Foley type catheter having an exterior surface, and first and second pairs of ring electrodes formed on the exterior surface of the Foley catheter. Each of the first and second pairs of ring electrodes is configured to perform at least one of stimulating the nerve and recording nerve activity.

The apparatus according to one embodiment includes at least one conductor coupled to the first and second pairs of ring electrodes that is configured to carry signals between the first and second pairs of ring electrodes and a processing apparatus. In one embodiment, the first and second pairs of ring electrodes each comprise an anode ring electrode and a cathode ring electrode. The second pair of ring electrodes is configured to deliver bipolar nerve stimulation, and the first pair of ring electrodes is configured to provide bipolar recording of nerve activity.

The apparatus according to one embodiment includes a third pair of ring electrodes formed on the exterior surface of the Foley catheter, wherein the third pair of ring electrodes is configured to perform at least one of stimulating the nerve and recording nerve activity. In one embodiment, the first pair of ring electrodes includes first and second ring electrodes that are separated by a distance of about 5 mm to 10 mm, and the second pair of ring electrodes includes third and fourth ring electrodes that are separated by a distance of about 5 mm to 10 mm, and wherein the third pair of ring electrodes includes fifth and sixth ring electrodes that are separated by a distance of about 5 mm to 10 mm. In one embodiment, a center of the first pair of ring electrodes is separated from a center of the second pair of ring electrodes by a distance of about 18 mm to about 22 mm, and a center of the second pair of ring electrodes is separated from a center of the third pair of ring electrodes by a distance of about 18 mm to about 22 mm. In one embodiment, the third pair of ring electrodes is most distally positioned on the Foley catheter, and the third pair of ring electrodes is positioned proximally from a proximal end of a balloon of the Foley catheter by a distance of about 35-40 mm.

In one embodiment, the first pair of ring electrodes includes first and second ring electrodes that are separated by a distance of about 5 mm to 10 mm, and the second pair of ring electrodes includes third and fourth ring electrodes that are separated by a distance of about 5 mm to 10 mm. In one embodiment, a center of the first pair of ring electrodes is separated from a center of the second pair of ring electrodes by a distance of about 8 mm to about 12 mm. In one embodiment, the second pair of ring electrodes is most distally positioned on the Foley catheter, and the second pair of ring electrodes is positioned proximally from a proximal end of a balloon of the Foley catheter by a distance of about 47-57 mm.

In one embodiment, a center of the first pair of ring electrodes is separated from a center of the second pair of ring electrodes by a distance of about 10.5 mm to about 14.5 mm. In one embodiment, the second pair of ring electrodes is most distally positioned on the Foley catheter, and wherein the second pair of ring electrodes is positioned proximally from a proximal end of a balloon of the Foley catheter by a distance of about 68-78 mm.

In one embodiment, a third pair of ring electrodes is formed on the exterior surface of the Foley catheter, wherein the third pair of ring electrodes is configured to perform at least one of stimulating the nerve and recording nerve activity, wherein the third pair of ring electrodes is most distally positioned on the Foley catheter, and wherein the third pair of ring electrodes is positioned proximally from a proximal end of a balloon of the Foley catheter by a distance of about 5-15 mm.

In one embodiment, at least one of the first and second pairs of ring electrodes is configured to be used for spontaneous recording during surgical dissection. In one embodiment, at least one of the first and second pairs of ring electrodes is configured to provide therapeutic stimulation.

Another embodiment is directed to a method of monitoring nerve activity. The method includes deploying a Foley type catheter in a urethra of a human patient, wherein the Foley type catheter comprises a first pair of ring electrodes and a second pair of ring electrodes. The method includes stimulating a nerve, and recording nerve activity resulting from the stimulation with at least one of the first and second pairs of ring electrodes.

In one embodiment, the method further includes positioning the second pair of ring electrodes at a membranous urethra of the human patient for the stimulation. The method according to one embodiment further includes calculating a nerve conduction velocity based on the recorded nerve activity, identifying a nerve fiber type corresponding to the calculated nerve conduction velocity, and displaying the identified nerve fiber type on a monitor coupled to the Foley type catheter. In one embodiment, the Foley type catheter includes a third pair of ring electrodes, and the method further includes performing at least one of stimulating the nerve and recording nerve activity with the third pair of ring electrodes.

Yet another embodiment is directed to a system for monitoring a nerve from a urethra of a patient. The system includes a Foley type catheter configured to be deployed in the urethra and comprising a first pair of ring electrodes and a second pair of ring electrodes. Each of the first and second pairs of ring electrodes is configured to perform at least one of stimulating the nerve and recording nerve activity. The system includes a monitor apparatus in communication with the first and second pairs of ring electrodes to process the recorded nerve activity. In one embodiment, the Foley type catheter further includes a third pair of ring electrodes configured to perform at least one of stimulating the nerve and recording nerve activity.

While the incidence of erectile dysfunction has decreased significantly in the last 10 years, there is still an unmet need. The periprostatic nerves are too small to see, even with 20× endoscopic magnification, so the surgeons are literally blind to the nerve location, and the risk of erectile dysfunction is 10%-46% in robotic, and 14%-79% in open procedures. Embodiments disclosed herein can be used during nerve sparing radical prostatectomy surgery or other pelvic surgeries to help surgeons locate the nerves, reducing the risk of nerve injury and erectile dysfunction. Embodiments disclosed herein can be used for open, laparoscopic, and robotic pelvic procedures. For post operation recovery, one pair of the electrodes is used to stimulate nerves, which can help the recovery of nerves that were stretched during the surgery.

In one embodiment, a Foley catheter with two pairs of ring electrodes is used in female pelvic surgical procedures. The first pair is 4.5 cm from the pair center to the proximal side of the balloon, and the second pair is located 2.5 cm from the pair center to the proximal side of the balloon. The pair closest to the membranous urethra is used to either stimulate nerves or record nerve action potentials. This design allows for locating (mapping) nerves within the pelvis, recording spontaneous nerve action potentials, or therapeutic stimulation of the nerves intraoperatively or postoperatively to facilitate nerve recovery or functional improvement in the event of iatrogenic nerve injury or irritation.

Although the present disclosure has been described with reference to preferred embodiments, workers skilled in the art will recognize that changes can be made in form and detail without departing from the spirit and scope of the present disclosure.

What is claimed is:

1. An apparatus for monitoring a nerve, comprising:
   a Foley type catheter having an exterior surface;
   first and second pairs of ring electrodes formed on the exterior surface of the Foley catheter, wherein the second pair of ring electrodes delivers bipolar nerve stimulation, and the first pair of ring electrodes provides bipolar recording of nerve activity;
   a processing apparatus to process the recorded nerve activity; and
   a first conductor coupled to the processing apparatus and the first pair of ring electrodes to carry signals representing the recorded nerve activity to the processing apparatus.

2. The apparatus of claim 1, and further comprising:
   a second conductor coupled to the processing apparatus and the second pair of ring electrodes and configured to carry signals between the second pair of ring electrodes and the processing apparatus.

3. The apparatus of claim 1, wherein the first and second pairs of ring electrodes each comprise an anode ring electrode and a cathode ring electrode.

4. The apparatus of claim 1, and further comprising:
   a third pair of ring electrodes formed on the exterior surface of the Foley catheter, wherein the third pair of ring electrodes is configured to perform at least one of stimulating the nerve and recording nerve activity.

5. The apparatus of claim 4, wherein the first pair of ring electrodes includes first and second ring electrodes that are separated by a distance of about 5 mm to 10 mm, and wherein the second pair of ring electrodes includes third and fourth ring electrodes that are separated by a distance of about 5 mm to 10 mm, and wherein the third pair of ring electrodes includes fifth and sixth ring electrodes that are separated by a distance of about 5 mm to 10 mm.

6. The apparatus of claim 5, wherein a center of the first pair of ring electrodes is separated from a center of the second pair of ring electrodes by a distance of about 18 mm to about 22 mm, and wherein a center of the second pair of ring electrodes is separated from a center of the third pair of ring electrodes by a distance of about 18 mm to about 22 mm.

7. The apparatus of claim 6, wherein the third pair of ring electrodes is most distally positioned on the Foley catheter, and wherein the third pair of ring electrodes is positioned proximally from a proximal end of a balloon of the Foley catheter by a distance of about 35-40 mm.

8. The apparatus of claim 1, wherein the first pair of ring electrodes includes first and second ring electrodes that are separated by a distance of about 5 mm to 10 mm, and wherein the second pair of ring electrodes includes third and fourth ring electrodes that are separated by a distance of about 5 mm to 10 mm.

9. The apparatus of claim 8, wherein a center of the first pair of ring electrodes is separated from a center of the second pair of ring electrodes by a distance of about 8 mm to about 12 mm.

10. The apparatus of claim 9, wherein the second pair of ring electrodes is most distally positioned on the Foley catheter, and wherein the second pair of ring electrodes is positioned proximally from a proximal end of a balloon of the Foley catheter by a distance of about 47-57 mm.

11. The apparatus of claim 8, wherein a center of the first pair of ring electrodes is separated from a center of the second pair of ring electrodes by a distance of about 10.5 mm to about 14.5 mm.

12. The apparatus of claim 11, wherein the second pair of ring electrodes is most distally positioned on the Foley catheter, and wherein the second pair of ring electrodes is positioned proximally from a proximal end of a balloon of the Foley catheter by a distance of about 68-78 mm.

13. The apparatus of claim 1, and further comprising:
a third pair of ring electrodes formed on the exterior surface of the Foley catheter, wherein the third pair of ring electrodes is configured to perform at least one of stimulating the nerve and recording nerve activity, wherein the third pair of ring electrodes is most distally positioned on the Foley catheter, and wherein the third pair of ring electrodes is positioned proximally from a proximal end of a balloon of the Foley catheter by a distance of about 5-15 mm.

14. The apparatus of claim 1, wherein at least one of the first and second pairs of ring electrodes is configured to be used for spontaneous recording during surgical dissection.

15. The apparatus of claim 1, wherein at least one of the first and second pairs of ring electrodes is configured to provide therapeutic stimulation.

16. A method of monitoring nerve activity, comprising:
deploying a Foley type catheter in a urethra of a human patient, wherein the Foley type catheter comprises a first pair of ring electrodes and a second pair of ring electrodes;
stimulating a nerve;
recording nerve activity resulting from the stimulation with at least one of the first and second pairs of ring electrodes; and
calculating a nerve conduction velocity based on the recorded nerve activity.

17. The method of claim 16, and further comprising:
positioning the second pair of ring electrodes at a membranous urethra of the human patient for the stimulation.

18. The method of claim 16, and further comprising:
identifying a nerve fiber type corresponding to the calculated nerve conduction velocity.

19. The method of claim 18, and further comprising:
displaying the identified nerve fiber type on a monitor coupled to the Foley type catheter.

20. A system for monitoring a nerve from a urethra of a patient, the system comprising:
a Foley type catheter configured to be deployed in the urethra and comprising a first pair of ring electrodes and a second pair of ring electrodes, wherein each of the first and second pairs of ring electrodes records nerve activity; and
a monitor apparatus in communication with the first and second pairs of ring electrodes to process the recorded nerve activity.

21. The system of claim 20, wherein the Foley type catheter further comprises:
a third pair of ring electrodes configured to perform at least one of stimulating the nerve and recording nerve activity.

* * * * *